United States Patent [19]

Borsotti et al.

[11] Patent Number: 5,432,269
[45] Date of Patent: Jul. 11, 1995

[54] PROCESS FOR PRODUCING ALKYL GLYCOSIDES

[75] Inventors: Giampietro Borsotti; Claudio Santini, both of Novara; Luigi Nataloni, Bologna; Tullio Pellizzo, Paderno Dugnano, all of Italy

[73] Assignees: Enichem S.p.A.; Eniricerche S.p.A., Milan, Italy

[21] Appl. No.: 59,808

[22] Filed: May 7, 1993

[30] Foreign Application Priority Data

May 15, 1992 [IT] Italy ................ MI92A1157

[51] Int. Cl.$^6$ .................. C07H 1/00; C08B 37/00
[52] U.S. Cl. .................... 536/18.6; 536/4.1; 536/18.5
[58] Field of Search ............ 536/4.1, 18.5, 120, 536/124, 18.6

[56] References Cited

U.S. PATENT DOCUMENTS

| H619 | 4/1989 | McDaniel, Jr. et al. | 536/18.6 |
|---|---|---|---|
| 4,152,513 | 5/1979 | Austin et al. | 536/4 |
| 4,713,436 | 12/1987 | Downs et al. | 528/295.3 |

FOREIGN PATENT DOCUMENTS

| 0077167 | 4/1983 | European Pat. Off. . |
|---|---|---|
| 0132046 | 1/1985 | European Pat. Off. . |
| 4040656 | 6/1992 | Germany . |
| 90/07516 | 7/1990 | WIPO . |

OTHER PUBLICATIONS

"M-PYROL © N-Methyl-2-Pyrrolidone Handbook", GAF Corporation Chemical Division, New York, 1972, Chapters 1–2.

*Primary Examiner*—Douglas W. Robinson
*Assistant Examiner*—Kathleen Kahler Fonda
*Attorney, Agent, or Firm*—Rogers & Wells

[57] ABSTRACT

A process is disclosed for preparing alkyl glycosides of general formula (I), by reacting an alcohol with a reducing sugar or with an equivalent of the latter, in the presence of a binary catalyst formed by a strong organic acid and a weak, also organic, base, having a $K_a$ within the range of from $10^{-8}$ to $10^{-1}$.

14 Claims, 1 Drawing Sheet

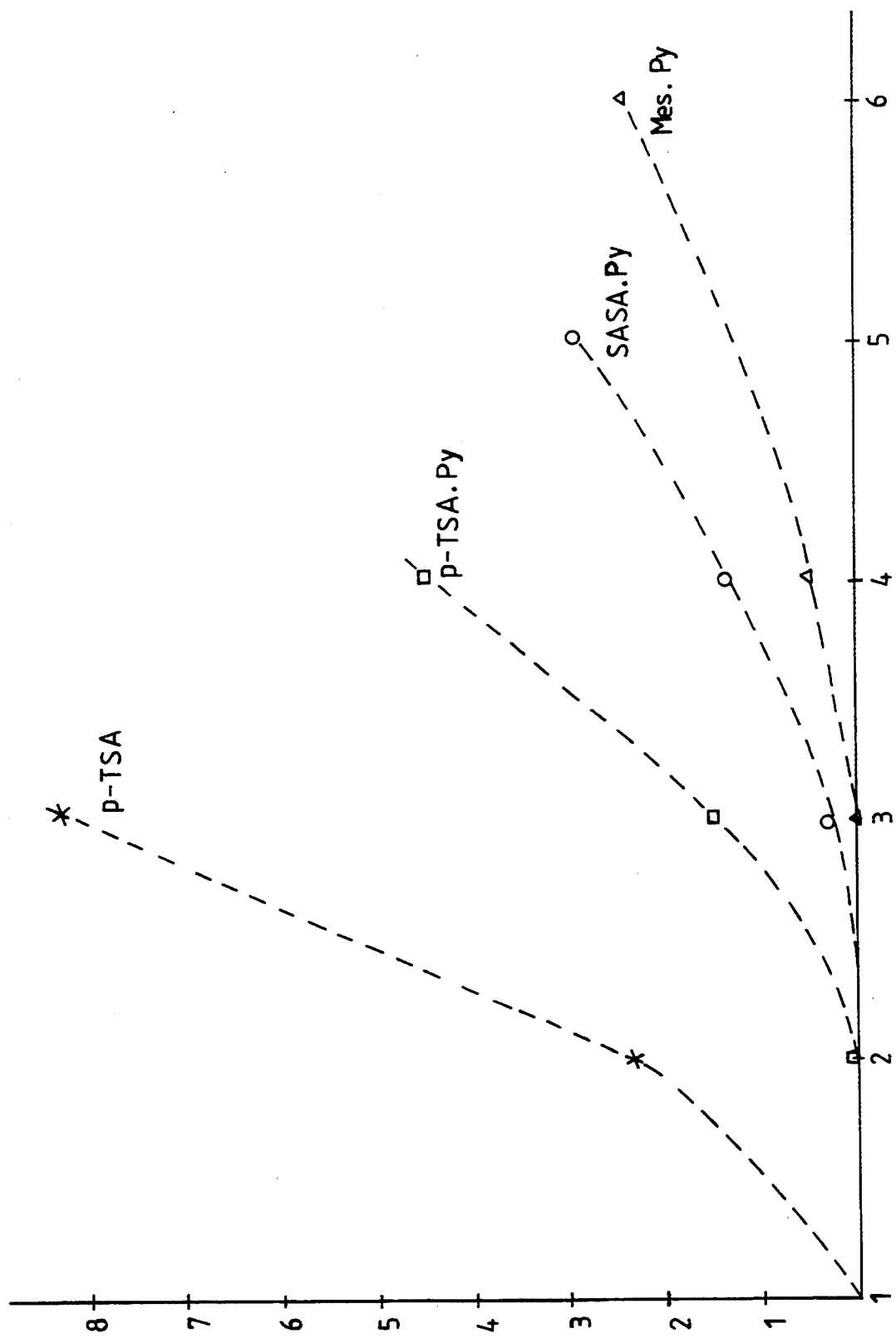

PROCESS FOR PRODUCING ALKYL GLYCOSIDES

The present invention relates to a process for preparing alkyl polyglucosides.

The field of surfactants has seen a considerable development during the past years; nowadays, a large share of the world market is constituted by non-ionic surfactants, and in particular, by polyethoxylated alcohols and polyethoxylated alkylphenols.

Such non-ionic surfactants have gained a considerable importance thanks to their good detergent properties, to their flexibility in the various formulations (compatibility with ionic surfactants) and to their low production cost.

Besides these classes of non-ionic surfactants, new classes have been developed recently, which are characterized by hydrophilic moieties different from polyethoxy groups; among these, the esters of mono- and oligosaccharides seem to be particularly attractive, owing to their low cost and intrinsic biodegradability.

However, these types of long chain esters, derived, e.g., from palmitic acid, are not satisfactory from a practical viewpoint, owing to the limited stability of the esters group at pH values higher than 8, necessary in a large number of formulations.

Such a limited chemical stability was overcome by introducing ether linkages resulting from the reaction of epoxides with a hydroxyethyl glucoside, as disclosed in Italian Patent Application No. MI-91A-001427, to the name of Erichem Augusta S.p.A..

Extremely good surfactants are also the alkyl-glucosides, whose preparation process has been widely disclosed in a large number of patents.

The problems connected with their preparation essentially are as follows:

(1) methods to prevent products from getting coloured;
(2) search for optimal catalyst;
(3) methods for neutralizing said catalyst;
(4) methods to facilitate the removal of the excess alcohol by distillation.

Regarding the catalyst, the use of p-toluenesulfonic acid, sulfuric acid and sulfonic resins was already disclosed in patents filed prior to the Seventies.

Recent developments are, for example, use of sulfosuccinic acid, as disclosed in WO 91/02742, and of dinonyl-naphthalene sulfonic acid, in WO 90/07516.

Regarding the problem of colour, a large number of patents exist which teach the use, besides the catalyst, of reducing acids (EP 77 167) or hydroxyacids (U.S. Pat. No. 4,465,828).

The resulting products, before being distilled in order to recover the excess alcohol, are neutralized with certain bases, as disclosed in 4,713,447 and EP 132 046.

Regarding distilling off the alcohol excess, in U.S. Pat. No. 4,510,306 and U.S. Pat. No. 4,889,925 the addition of fluidifier agents is disclosed in order to facilitate the stripping of the same alcohol.

In any case, the essential problem is the reduction of polyglucose, which, by causing an increase in product viscosity, makes it difficult for the alcohol to be removed.

In fact, in the presence of a large amount of polyglucose, the product is semisolid and this makes it impossible for thin-layer distillation techniques to be used.

In Patent WO 90/07516 a novel class of high-lipophilicity sulfonic acids is introduced, which considerably reduce the formation of polyglucose which, also considering the reaction economics, brings a loss of yield of desired product.

However, such catalysts have a high cost and must be purposely prepared.

The present Applicant has found that a glycosidation product can be obtained which is free from, or only contains extremely small amounts of, polyglucose, if the reaction is carried out in the presence of a particular catalytic system.

Therefore, the subject-matter of the present invention is a process for preparing alkyl glycosides of general formula (I):

$$H-(G)_n-O-R \qquad (I)$$

in which:

R is an alkyl of from 8 to 20 carbon atoms, which may be either linear or branched, saturated or unsaturated;

G is a glycosidic moiety resulting from the removal of a $H_2O$ molecule of a monosaccharide commonly referred to as "reducing sugar", typically a hexose or a pentose of formula $C_6H_{12}O_6$ or $C_5H_{10}O_5$;

n is an integer within the range of from 1 to 5;

said process comprising the reaction of an alcohol with a reducing sugar or an equivalent thereof, which may an alkyl glucoside or a compound capable of generating, in situ said reducing sugar, with said reaction being carried out in the presence of a binary catalyst formed by a strong organic acid and a weak, also organic, base, having a $K_a$ value within the range of from $10^{-8}$ to $10^{-1}$.

Examples of strong organic acids are: hindered alkylbenzenesulfonic acids, such as 2,4,6-trimethylbenzenesulfonic acid and 2,4,6-triisopropylbenzenesulfonic acid, secondary and tertiary alkylsulfonic acids, such as SASA, cyclohexanecarboxy-1-sulfonic acid, those 2-hydroxyalkylsulfonic acids which can be obtained, for example, from the internal epoxides by reaction with $NaHSO_3$ or the corresponding alcoxy derivatives which can be obtained from the same 2-hydroxyalkylsulfonic acids by alkylation.

Examples of weak organic bases are pyridine, picolines, lutidines, collidines, quinoline, isoquinoline, quinaldine, pyrazine, pteridine and tetramethylurea.

The catalyst can be easily prepared either separately or in situ by mixing equivalent amounts of said acids and bases.

Preferred catalysts are the salts of pyridine or quinoline with alkylbenzenesulfonic acids or secondary alkylsulfonic acids; the latter can be obtained, for example, according to Italian patent application No. 20 878 A/89 to the name of Enichem Augusta S.p.A., the contents of which are incorporated herein by reference.

Among all, preferred are the quinoline salts of mesitylene sulfonic (or 2,4,6-trimethylbenzenesulfonic) acid and of the secondary alkylsulfonic acids of from 14 to 17 carbon atoms (SASA).

The catalyst can be used in amounts within the range of from 0.001 to 0.1 mol per mol of reducing sugar or of an equivalent thereof, and preferably of from 0.01 to 0.05 mol.

The unique character of this catalyst is demonstrated by a comparison test disclosed in Example 3, in which the reaction is carried out in the presence of other catalysts, among which is a conventional acid, such as p-toluenesulfonic acid.

By operating under the same conditions of temperature, pressure and reaction mass stirring speed as in the test of Example 2 and collecting, every hour, identical samples of reaction product until the solution turns homogeneous and glucose disappears, meaningful differences may be observed, as evidenced by Chart 1, in the kinetics of formation of polyglucose as a reaction byproduct.

The end product, obtained with the binary catalyst according to the present invention, proves to be nearly completely free from polyglucose. This constitutes a typical feature of the present process, as compared to the prior art.

By using the catalysts disclosed hereinabove, a kinetic control of the reaction is more easily performed because, for example, products of formula (I) with a high level of alkyl-monoglucosides [(e.g., mixtures containing >70% of product with n=1 in formula (I)] can be obtained more easily.

Furthermore, when such binary catalysts are used, products with a much lighter colour are obtained at the end of the reaction, as compared to products obtained with conventional acidic catalysts such as, e.g., p-toluenesulfonic acid. Consequently, when the process is carried out under optimal conditions, decolorizing the end product is no longer necessary.

The basic component of the binary catalyst is easily liberated at the end of the reaction by adding at least one equivalent of a strong base which neutralizes the acid component of the binary catalyst.

The base is completely recovered during the step of distillation of alcohol excess.

The free base-containing alcoholic phase, after the addition of one equivalent of a strong acid, can be used again for a subsequent glycosidation, yielding the same results.

More particularly, the process according to the present invention comprises the reaction of a reducing sugar or of an equivalent thereof, which may be an alkyl glucoside or a compound capable of generating in situ said reducing sugar, with a monohydroxy alcohol of from 8 to 20 carbon atoms, in the presence of the binary catalyst as disclosed hereinabove, carried out at 90°–130° C. and with water being continuously removed as formed.

Reducing sugars suitable for the intended purpose are hexoses or pentoses, such as: glucose, mannose, galactose, arabinose, xylose, ribose and the like.

Also higher sugars or substituted saccharides can be used which can be hydrolysed yielding monosaccharides: among these are starch, maltose, saccharose, lactose, maltotriose, methyl-, ethyl-, or butyl-glucosides, and so forth.

Due to its low cost and large availability, the preferred monosaccharide is glucose.

Suitable alcohols for this reaction are the linear or branched, saturated or unsaturated primary or secondary alcohols.

Alcohol examples are octyl alcohol, decyl alcohol, dodecyl alcohol, tetradecyl alcohol, hexadecyl alcohol, oleyl alcohol and alcohols from oxosynthesis with a linear/branched ratio of 45:55, such as LIAL 111, LIAL 123, LIAL 145 or fractions of linear alcohols obtained from the latter by crystallization (ALCHEM 111, 123, 145).

The alcohol is used in an amount equal to, or larger than, the stoichiometric amount of the reducing sugar or of its equivalent, and namely within the range of from 1:2 to 1:10 and preferably of from 1:3 to 1:6.

The selected value of the molar ratio conditions the characteristics of the end product of formula (I); so, if a product with a high polymerization degree (n) is desired, the reaction will be carried out at such low ratios as 1:2, whereas if a product prevailingly containing alkyl-monoglucoside (n=1) is desired, such high ratios as 1:6 will be used.

The alcohol performs the additional function of a reaction solvent.

The reaction temperature is within the range of from 90° to 130° C.; it is preferably within the range of from 110° to 120° C.

In order to obtain large amounts of alkyl-monoglucosides [formula (I) with n=1], discontinuing the reaction when carbohydrate conversion is not complete may prove advantageous.

In this case, in order that the unreacted carbohydrate be more easily recovered, diluting the reaction mixture with a solvent in which said carbohydrate is insoluble, such as hexane, heptane or toluene may prove suitable.

Such an operation also offers the additional advantage of yielding a more fluid reaction mixture, hence more easily separable by carbohydrate filtration.

At the end of the reaction, at least one mol of a strong base is added to the reaction mixture per each mol of catalyst used.

By "strong bases" the alkali metal or alkaline-earth metal hydroxides and alkali metal alkoxides are understood.

Preferred bases are sodium hydroxide and sodium methoxide.

During this step, the weak organic base used, such as quinoline, is liberated from the strong acid and during the subsequent distillation step, it is recovered together with the alcohol and can hence be used again in another cycle.

Any unreacted alcohol is then distilled off under a residual pressure of 0.1–0.5 mmHg, with a kettle temperature of 160°–180° C.

Such a distillation can be carried out with a traditional apparatus or, preferably, with a thin layer evaporator.

The residue obtained from said distillation can be used as such or it cam possibly be dissolved in water, for example by using an equal volume of water as compared to said residue, in order to obtain a solution at 50% by weight/weight (w/w).

The following examples are supplied for merely illustrative purposes, and in no way shall be construed as being limitative of the present invention.

EXAMPLE 1

500 g of 1-dodecanol and 90 g of anhydrous glucose are charged to a flask of 1 liter of capacity equipped with stirrer, thermometer and distillation head.

The mixture is heated up to 118°–120° C. and then 1.95 g is added of quinoline salt of mesitylene sulfonic acid (Mes.Q).

The reaction equipment is connected with a vacuum pump and the internal system pressure is reduced down to approximately 25 mmHg.

Heating is continued until the formation of $H_2O$ ends with, after about 4 hours, a slightly opalescent solution being obtained.

An aliquot of the raw reaction mixture, dissolved in isopropanol: $H_2O=1:1$, has an extinction at 470 nm of 0.6 ($E_{470}=0.6$).

0.4 g of $CH_3ONa$ is added and the reaction mixture is distilled under the reduced pressure of 0.1 mmHg in a thin-layer evaporator Leybold-Herans Mod KDL1 heating at 170°–180° C.

425 g of 1-dodecanol are recovered, which contain the amount of quinoline corresponding to the initially used catalyst, which hence can be used again in subsequent tests.

The residue is a glass-like, slightly coloured product weighing 150 g; when analyzed by HPLC (high pressure Liquid chromatography) and by GC (gas chromatography) after preliminary silanation, it results to have the following composition:

| | |
|---|---|
| dodecyl monoglucoside = | 75.0% |
| dodecyl diglucoside = | 14.8% |
| dodecyl triglucoside = | 4.9% |
| dodecyl tetraglucoside = | 2.1% |
| dodecyl pentaglucoside = | 1.3% |
| glucose = | absent |
| polyglucose = | 0.7% |
| dodecanol = | 0.5% |

EXAMPLE 2

500 g of alcohols LIAL 123 (linear and branched $C_{12}$ and $C_{13}$ oxo alcohols with linear:branched ratio=45:55) and 90 g of anhydrous glucose are charged to the same equipment as in Example 1.

The mixture is heated up to 118°–120° C. and then 1.95 g of quinoline salt of mesitylene sulfonic acid are added.

By operating as in Example 1, after 6 hours a slightly opalescent solution is obtained.

The extinction of an aliquot of the raw reaction mixture dissolved in isopropanol:$H_2O=1:1$ is 1.0 ($E_{470}=1$).

0.4 g of $CH_3ONa$ is added and the reaction mixture is distilled under the reduced pressure of 0.1 mmHg, in a thin-layer evaporator Leybold-Herans Mod KDL1, heating at 180°–190° C.

The distillate is constituted by 428 g of alcohols LIAL 123 (containing quinoline) and the residue is constituted by 151 g of alkyl glycosides, as a glass-like, slightly coloured, solid product.

This residue, when analyzed by HPLC (high-pressure liquid chromatography) and GC (gas chromatography) after preliminary silanation, has the following composition:

| | |
|---|---|
| alkyl monoglucosides = | 72.2% |
| alkyl diglucosides = | 16.2% |
| alkyl triglucosides = | 5.9% |
| alkyl tetraglucosides = | 2.6% |
| alkyl pentaglucosides = | 1.3% |
| glucose = | absent |
| polyglucose = | 2.3% |
| free alcohols = | 0.5% |

EXAMPLE 3

Comparison test with different catalysts

Inside the same equipment of Example 1 and by operating with the same amounts of reactants and according to the same modalities, instead of the quinoline salt of mesitylenic acid (Mes.Q), equivalent amounts (0.0059 mols) were used of the following catalysts:

p-toluenesulfonic acid (PTS);
pyridinium p-toluenesulfonate (PTS.Py);
pyridinium 2,4,6-trimethylbenzenesulfonate (Mes.Py);
salt of secondary alkyl sulfonic acids (SA-SA.Py).

This latter catalyst was prepared as follows: 25 g of technical SASA, obtained by operating as disclosed in Italian patent application No.20878 A/89 to Enichem Augusta S.p.A. and constituted by 68% of secondary alkyl sulfonic acid with average molecular weight ($MW_{ave}$) 293, 8% of secondary alkyl disulfonic acid with $MW_{ave}$ 373, 8% of $H_2SO_4$, balance to 100% water, is treated with an excess of pyridine.

A syrup-like solution is obtained which is thoroughly dehydrated under reduced pressure at 100° C. in Rotavapor.

The residue is diluted with 100 cc of ethyl ether.

The formed precipitate, constituted by pyridinum sulfate, is filtered off, and the ethereal solution is concentrated again to dryness.

23 g are obtained of a light yellow paste which is used as such in the glucosidation reaction.

During the tests, samples consisting of equal amounts of reaction mixture were collected at constant time intervals of 1 hour.

Such samples were diluted with ethyl ether and extracted three times with water.

All the aqueous extracts were adjusted at a same volume and were analyzed, under the same conditions, by HPLC (high pressure liquid chromatography), using a Hypersil $C_{18}$ column with eluent $H_2O:CH_3CN$, gradient from 100% to 0% and Light Scattering detector.

The results, expressed as relative polyglucose surface areas as a function of time (hours) are reported in the accompaning chart.

From the latter, it can be clearly seen that by associating pyridine with p-TSA, the amount of polyglucose sharply decreases and such a decrease is even larger if the sulfonic group shielding action by the sterically hindering moieties increases.

We claim:

1. A process for preparing alkyl glycosides of general formula

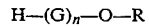

in which:
R is an alkyl group of from 8 to 20 carbon atoms, which may be either linear or branched, saturated or unsaturated;
G is a glycosidic moiety resulting from the removal of an $H_2O$ molecule of a monosaccharide reducing sugar;
n is an integer within the range of from 1 to 5;
said process comprising the reaction of an alcohol with a reducing sugar, an alkyl glycoside or a compound capable of generating, in situ, said reducing sugar, wherein said reaction is carried out in the presence of a binary catalyst formed by a strong organic acid and a weak organic base, selected from the group consisting of pyridine, picolines, lutidines, collidines, quinoline, isoquinoline, quinaldine, pyrazine, pteridine, and tetramethylurea, said weak organic base having a $K_a$ value within the range of from $10^{-8}$ to $10^{-1}$, with the proviso that the binary catalyst is within the range of from 0.001 to 0.1 mol per mol of the reducing sugar, alkyl glycoside, or compound capable of generating, in situ, said reducing sugar.

2. The process according to claim 1, in which the strong organic acid of the binary catalyst is selected from the group consisting of alkylbenzenesulfonic acids and secondary and tertiary alkylsulfonic acids.

3. The process according to claim 2, in which the alkylbenzenesulfonic acid is 2,4,6-trimethylbenzenesulfonic acid or 2,4,6-triisopropylbenzene-sulfonic acid.

4. The process according to claim 2, in which the secondary and tertiary alkylsulfonic acids are secondary alkylsulfonic acids, cyclohexanecarboxy-1sulfonic acid, 2-hydroxy-alkylsulfonic or 2-alkoxy-alkylsulfonic acids.

5. The process according to claim 1, in which the binary catalyst is selected from the group consisting of pyridine or quinoline salts of alkylbenzenesulfonic acids, or pyridine or quinoline salts of secondary alkylsulfonic acids.

6. The process according to claim 5, in which the binary catalyst is the quinoline salt of mesitylenesulfonic acid or of a and secondary alkylsulfonic acid containing from 14 to 17 carbon atoms.

7. The process according to claim 6, in which the binary catalyst is the quinoline salt of mesitylenesulfonic.

8. The process according to claim 1, in which the binary catalyst is prepared by mixing equivalent amounts said a strong organic acid and said weak organic base.

9. The process according to claim 1, in which the binary catalyst is used in an amount within the range of from 0.01 to 0.05 mol per mol of reducing sugar, alkyl glycoside or compound capable of generating said reducing sugar in situ.

10. The process according to claim 1, in which the molar ratio of the reducing sugar, alkyl glycoside or compound capable of generating said reducing sugar in situ to the alcohol is within the range of from 1:2 to 1:10.

11. The process according to claim 10, in which the molar ratio of the reducing sugar, alkyl glycoside or compound capable of generating said reducing sugar in situ to the alcohol is within the range of from 1:3 to 1:6.

12. The process according to claim 1, in which the alcohol is used as a reaction solvent.

13. The process according to claim 1, in which the reaction temperature is within the range of from 90° to 130° C.

14. The process according to claim 13, in which the reaction temperature is within the range of from 100° to 120° C.

* * * * *